US005766622A

United States Patent [19]
Nelson

[11] Patent Number: 5,766,622
[45] Date of Patent: Jun. 16, 1998

[54] INHIBITING UNDESIRABLE TASTE IN ORAL COMPOSITIONS

[75] Inventor: Sandra Lynn Nelson, Loveland, Ohio

[73] Assignee: The Procter & Gamble Company, Cincinnati, Ohio

[21] Appl. No.: 696,711

[22] Filed: Aug. 14, 1996

[51] Int. Cl.$^6$ ................................................. A61K 31/74
[52] U.S. Cl. ............................ 424/440; 441/48; 441/49; 441/54; 514/974
[58] Field of Search ............................... 424/440, 441, 424/48, 49, 54; 514/974

[56] References Cited

U.S. PATENT DOCUMENTS

| | | | |
|---|---|---|---|
| 3,140,978 | 7/1964 | Zentner | 167/55 |
| 4,154,862 | 5/1979 | Guadagni et al. | 426/536 |
| 4,248,141 | 2/1981 | Miller, Jr. | 99/483 |
| 4,282,264 | 8/1981 | Magnolato | 426/599 |
| 4,465,662 | 8/1984 | Sato et al. | 424/54 |
| 4,517,379 | 5/1985 | Brennan et al. | 564/193 |
| 4,581,232 | 4/1986 | Peters et al. | 424/155 |
| 4,994,490 | 2/1991 | Roy et al. | 514/522 |
| 5,009,819 | 4/1991 | Popescu et al. | 264/4.1 |
| 5,015,628 | 5/1991 | Reynolds | 514/12 |
| 5,024,997 | 6/1991 | Motola et al. | 514/58 |
| 5,192,563 | 3/1993 | Patel et al. | 426/5 |
| 5,232,735 | 8/1993 | Kurtz et al. | 426/649 |
| 5,262,179 | 11/1993 | Gregory et al. | 424/489 |
| 5,266,717 | 11/1993 | Roy et al. | 558/413 |
| 5,286,489 | 2/1994 | Tsau | 424/440 |
| 5,336,513 | 8/1994 | Riemer | 426/548 |
| 5,350,839 | 9/1994 | Asaka et al. | 536/7.4 |
| 5,407,921 | 4/1995 | Katsuragi et al. | 514/75 |
| 5,439,671 | 8/1995 | Ansmann et al. | 424/56 |
| 5,580,545 | 12/1996 | Wahino | 424/49 |

FOREIGN PATENT DOCUMENTS

| | | |
|---|---|---|
| 0551820 A1 | 7/1993 | European Pat. Off. . |
| 0 635 218 A1 | 1/1995 | European Pat. Off. . |
| 5-4921 | 1/1991 | Japan . |
| 4-9335 | 1/1992 | Japan . |
| 4-207161 | 7/1992 | Japan . |
| 5-15389 | 1/1993 | Japan . |
| 5-84288 | 12/1993 | Japan . |
| 2508547 | 6/1996 | Japan . |
| 2508555 | 6/1996 | Japan . |
| WO 93/10677 | 6/1993 | WIPO . |

OTHER PUBLICATIONS

"Specific Inhibitor for Bitter Taste", Nature, vol. 365 (Sep. 16, 1993), pp. 213–214.
Roy, G., "The Applications and Future Implications of Bitterness Reduction and Inhibition in Food Products", Food Science and Nutrition, vol. 29, Issue 2 (1990), pp. 59–71.
Roy, G., "Taste Masking in Oral Pharmaceuticals", Pharmaceutical Technology (Apr., 1994), pp. 84–99.
Roy, G., "Bitterness Reduction and Inhibition", Trends in Food Science & Technology, vol. 3 (Apr., 1992), pp. 85–91.

*Primary Examiner*—Joseph L. Schofer
*Assistant Examiner*—D. Faulkner
*Attorney, Agent, or Firm*—Douglas C. Mohl; T. David Reed; Mary Catherine Hentz

[57] ABSTRACT

The present invention relates to a method for inhibiting an undesirable taste in oral compositions such as foods, beverages, and pharmaceuticals. The present invention also relates to oral and pharmaceutical compositions comprising undesirable tasting compounds wherein undesirable tastes are inhibited by the addition of a phosphorylated amino acid, such as phosphotyrosine, phosphoserine, phosphothreonine, and mixtures thereof, to said oral and pharmaceutical compositions.

15 Claims, No Drawings

INHIBITING UNDESIRABLE TASTE IN ORAL COMPOSITIONS

TECHNICAL FIELD

The present invention relates to a method for inhibiting an undesirable taste in oral compositions such as foods, beverages, and pharmaceuticals. The present invention also relates to oral and pharmaceutical compositions comprising undesirable tasting compounds wherein said tastes are inhibited by the addition of a phosphorylated amino acid to said compositions.

BACKGROUND OF THE INVENTION

Consumers do not care for the taste modality of bitterness in the broadest sense. Therefore, the desire for improved palatability of oral compositions having a bitter taste has prompted the development of numerous formulations and methods of bitterness reduction/inhibition.

In most cases, the consumer or producer have attempted to mask the bitter attributes of various oral compositions by using compounds or mixtures of compounds, such as flavors and sugars or other sweetening ingredients. Gelatin (Japanese Patent Application No. 04-346,937); gelatinized starch (Japanese Patent Application No. 04-235,136); acidic amino acids (U.S. Pat. No. 4,517,379 and Japanese Patent Application Nos. 05-015,389 and JP 05-004,921); chitosan (Japanese Patent Application No. 04-009,335); cyclodextrins (U.S. Pat. No. 5,024,997); liposomes (U.S. Pat. No. 5,009,819); lecithin or lecithin like substances (Japanese Patent Application No. 62-265,234); surfactants (U.S. Pat. No. 5,439,671); salts (U.S. Pat. No. 5,262,179); and the like have also been used to mask unpleasant tastes in oral compositions. Likewise, coating or microencapsulation (European Patent Application No. 551,820); functional group alteration (U.S. Pat. No. 5,350,839); and structural matrix forms of taste masking have been used. Oral compositions employing such technology have incorporated agents such as silicate clays (U.S. Pat. Nos. 3,140,978 and 4,581,232); acrylic acid copolymers (U.S. Pat. No. 5,286,489); gums (U.S. Pat. No. 5,288,500); cellulose (U.S. Pat. No. 5,192,563); and waxes in an effort to further provide improved tasting compositions. Unfortunately masking bitter taste with such compounds, in effect masks the true overall flavor of the oral compositions.

Other methods of inhibiting/reducing bitter taste have also been disclosed. For example, Kurtz and Fuller have disclosed (U.S. Pat. No. 5,232,735 and PCT Application No. WO 93/10677) modifying certain compounds, such that they become tasteless, which when added to a composition comprising an undesirable taste, the undesirable taste is blocked. Roy, et al., have disclosed N-(sulfomethyl)-N'-arylureas as sweetness and bitterness inhibitors (U.S. Pat. Nos. 4,994,490 and 5,266,717). Guadagni, et al. have found that the addition of the flavone, neodiosmin, results in reduced bitterness and off-after-taste (U.S. Pat. No. 4,154,862), while Riemer has discovered that certain cinnamic acid derivatives have the ability to inhibit the taste of bitter compounds and the after taste of artificial sweeteners (U.S. Pat. No. 5,336,513). Magnolato has claimed a process for removing bitter taste from fruit and vegetable extracts by selective absorption using an inexpensive natural ligneous material (U.S. Pat. No. 4,282,264) and Miller has used steam to remove the bitter taste from soybeans (U.S. Pat. No. 4,248,141).

An ideal solution to bitterness reduction would be the development of a universal bitterness inhibitor that does not affect the overall flavor of the oral compositions. Katsuragi and Kurihara have reported in Nature, vol. 365, pp. 213-214, 1993, a bitterness inhibitor made of phosphatidic acid and β-lactoglobulin which suppresses taste responses and sensations to bitter substances without affecting the responses to other taste stimuli. Unfortunately, such a compound has only shown limited success in inhibiting the bitter taste in many different bitter tasting compounds.

The present inventor has discovered that the addition of a phosphorylated amino acid, such as phosphotyrosine, phosphoserine, phosphothreonine, and mixtures thereof, to oral compositions having an undesirable taste, such as bitter and/or metallic taste, inhibits said taste without substantially affecting the overall true taste of the compositions.

It is therefore an object of the present invention to provide a method for inhibiting the undesirable taste of oral compositions, such as foods, drinks, over-the-counter and prescription pharmaceuticals, and toiletries, by the addition of a phosphorylated amino acid to said compositions.

It is also an object of the present invention to provide pleasant tasting pharmaceutical compositions for treating cough/cold symptoms comprising at least one pharmaceutical active having an undesirable taste, and a safe and effective amount of a phosphorylated amino acid.

It is a further object of the present invention to provide pleasant tasting oral compositions such as dentifrices, mouthwashes, and the like comprising compounds having a bitter and/or metallic taste and a safe and effective amount of a phosphorylated amino acid.

It is a still further object of the present invention to provide pleasant tasting oral compositions for relief of gastrointestinal distress comprising compounds having a bitter and/or metallic taste and a safe and effective amount of a phosphorylated amino acid.

These and other objects of the invention will become readily apparent from the detailed description which follows.

SUMMARY OF THE INVENTION

The present invention relates to a method for inhibiting undesirable taste, such as bitter and/or metallic taste, comprising the addition of a safe and effective amount of a phosphorylated amino acid, including, but not limited to, phosphotyrosine, phosphoserine, phosphothreonine, and mixtures thereof, to oral compositions such as foods, drinks, pharmaceuticals, and toiletries.

The present invention also relates to pleasant tasting pharmaceutical compositions for treating cough/cold symptoms comprising at least one pharmaceutical active having a bitter and/or metallic taste, and a safe and effective amount of a phosphorylated amino acid; pleasant tasting oral compositions such as dentifrices, mouthwashes, and the like, comprising compounds having a bitter and/or metallic taste and a safe and effective amount of a phosphorylated amino acid; and pleasant tasting oral compositions for relief of gastrointestinal distress comprising compounds having a bitter and/or metallic taste and a safe and effective amount of a phosphorylated amino acid.

All percentages and ratios used herein are by weight of the total composition, and all measurements made at 25° C., unless otherwise specified.

DETAILED DESCRIPTION OF THE INVENTION

The present invention comprises a method for inhibiting undesirable taste by adding a safe and effective amount of a phosphorylated amino acid including, but not limited to, phosphotyrosine, phosphoserine, phosphothreonine, and mixtures thereof, to oral compositions such as foods, drinks, pharmaceuticals, and toiletries. The present invention also comprises pleasant tasting pharmaceutical compositions for treating cough/cold symptoms comprising at least one pharmaceutical active having a bitter and/or metallic taste, and a safe and effective amount of a phosphorylated amino acid; pleasant tasting oral compositions such as dentifrices, mouthwashes, and the like comprising compounds having a bitter and/or metallic taste and a safe and effective amount of a phosphorylated amino acid; and pleasant tasting oral compositions for relief of gastrointestinal distress comprising compounds having a bitter and/or metallic taste and a safe and effective amount of a phosphorylated amino acid.

The phrase "oral compositions", as used herein, is defined as any product which in the ordinary course of usage is intentionally swallowed, such as foods, drinks, over-the-counter and/or prescription pharmaceuticals, and the like. However, the phrase "oral compositions", as used herein, is also intended to include the phrase "dental compositions", which as used herein, means any composition used in the oral cavity and/or to clean the teeth, and which is intentionally not swallowed but rather retained in the oral cavity for a time and then substantially expectorated, such as gums, toothpastes, dentifrices, mouthwashes, and the like.

The phrase "undesirable taste", as used herein, is not limited by the basic tastes of sweet, sour, bitter, umami, and salty; but is defined as any taste, including sweet, bitter, sour, alkaline, astringent, tangy, dry, sharp, cool, hot, burning, acidic, spicy, pungent, woody, smoky, umami, metallic, and/or any aftertaste, if such taste is unwanted in a composition.

The term "inhibit", as used herein, is defined as the slowing or interference of the taste transduction mechanism such that, while an undesirable tasting compound remains unchanged within a composition, the perception of the undesirable taste of the compound is decreased in the person or animal consuming said composition.

The term "mask", as used herein, is defined as covering, disguising, and/or obscuring an undesirable taste by the addition of compounds such as sweeteners, flavors, and the like, to compositions having an undesirable tasting compound, wherein the undesirable tasting compound remains unchanged, but its taste is overwhelmed by the other tastes present in the composition such that the undesirable taste is not perceived by the person or animal consuming said composition.

The phrase "chemical alteration", as used herein, is defined as the structural modification of a chemical compound having an undesirable taste such that the compound no longer has as undesirable taste.

The phrase "safe and effective amount", as used herein, is defined as an amount of a substance sufficient to provide the desired benefit without undue adverse side effects, such as toxicity, irritation, or allergic response, commensurate with a reasonable benefit/risk ratio when used in the manner of this invention.

The term "compatible", as used herein, is defined as that the components of the compositions are capable of being co-mingled with one another without substantially reducing the efficacy of the components or the composition under ordinary use conditions.

The term "dentifrice", as used herein, is defined as any composition, including toothpowders, toothpastes, toothgels, or liquids, which are generally used when brushing the teeth.

The phrase "phosphorylated amino acid", as used herein, is defined as the phosphorylated amino acids including, but not limited to, phosphotyrosine, phosphoserine, and phosphothreonine. The phrase, as used herein, is also intended to include: peptides of from about 2 to about 15 phosphorylated amino acids comprising phosphotyrosine, phosphoserine, phosphothreonine, and mixtures thereof, the dextro- or levo-rotatory isomers of these phosphorylated amino acids or racemic mixtures thereof, the physiologically acceptable salts thereof, the esters thereof, and derivatives of said phosphorylated amino acids comprising akyl chains (straight and branched chains, C1–C18), acyl chains (straight and branched chains, C1–C18), aryl groups, esters of the acid portion with straight and branched chains, C1–C18, substituted amino acids containing halogen, thio, cyano, and nitro groups, added to the amino acid. These and other modifications to the phosphorylated amino acids which would be obvious to one of ordinary skill in the chemical arts, are intended to be included within the scope of the present invention.

The phrase "pharmaceutically-acceptable carrier materials", as used herein, means one or more compatible solid or liquid filler diluents or encapsulating substances which are suitable for oral and/or nasal administration to a human or lower animal. Pharmaceutically-acceptable carrier materials must, of course, be of sufficiently high purity and sufficiently low toxicity to render them suitable for administration to the human being treated.

The phrase "orally-acceptable carrier materials", as used herein, means any material safe and effective for use in the dental compositions of the present invention. Such materials include but are not limited to, thickening materials, humectants, water, buffering agents, abrasive polishing materials, sodium bicarbonate, titanium dioxide, surfactants, flavors, sweeteners, coloring agents, coolants, and mixtures thereof.

Method Of Inhibiting Undesirable Taste:

Within the scope of the present invention the phosphorylated amino acids operate by inhibiting the perception of bitter and/or metallic taste. Thus, when the phosphorylated amino acids are added to oral compositions containing compounds which cause bitter and/or metallic taste, the oral compositions taste less bitter/metallic than similar oral compositions without the phosphorylated amino acids. The amount of the phosphorylated amino acids to be added to the oral compositions depends on various factors such as the nature of the composition, the concentration therein of the compound or compounds responsible for the undesirable taste, and the degree of inhibition desired. While it has been found that the preferred phosphorylated amino acids comprise phosphotyrosine, phosphoserine, phosphothreonine, and mixtures thereof, other phosphorylated amino acids may also be useful in inhibiting undesirable taste. The most preferred phosphorylated amino acid of the present invention is phosphotyrosine. It has also been found that useful results are typically obtained by adding from about 0.001% to about 10% by weight, preferably from about 0.01% to about 8% by weight, more preferably from about 0.1% to about 5% by weight, and most preferably from about 0.5% to about 2% by weight, of the phosphorylated amino acid to the oral compositions having an undesirable taste.

The oral compositions having an undesirable taste for which inhibition is desired are prepared simply by incorporating the phosphorylated amino acids therewith. The methods, as well as the compositions, for inhibiting undesirable taste by the addition of the phosphorylated amino acids of the present invention is further described below with reference to foods, drinks, and pharmaceuticals, respectively.

Examples of foods having an undesirable or bitter taste include, but are not limited to, citrus fruits such as grapefruit, orange, and lemon; vegetables such as tomato, pimento, celery, melon, carrot, potato, and asparagus; seasoning or flavoring materials such as flavor, sauces, soy sauce, and red pepper; foods originating from soybean; emulsion foods such as cream, dressing, mayonnaise, and margarine; processed marine products such as fish meat, ground fish meat, and fish eggs; nuts such as peanuts; fermented foods such as fermented soybean; meats and processed meats; pickles; noodles; soups including powdery soups; dairy products such as cheese; breads and cakes; confectioneries such as candies, chewing gum, and chocolate; and specifically prepared foods for health.

Examples of the drinks having an undesirable or bitter taste include juices of citrus fruits and vegetables, soybean milk, coffee, cocoa, black tea, green tea, fermented tea, semi-fermented tea, refreshing drinks, beverages, and milk.

Examples of pharmaceutical compositions having an undesirable or bitter/metallic taste include, but are not limited to, cough/cold oral compositions, dental compositions and compositions for treating the oral cavity, and compositions for treating gastrointestinal distress. There are no specific limitations with respect to the orally administrable pharmaceutical actives whose undesirable tastes can be suppressed by addition of the phosphorylated amino acids of the invention. However, these pharmaceutically acceptable actives should be compatible with the phosphorylated amino acids of the present invention, as well as other essential ingredients in the oral compositions. The phosphorylated amino acids of the present invention may also be used with mixtures of various pharmaceutical actives. Typical examples of the pharmaceutically acceptable actives which have an undesirable taste include actives selected from among the various groups of chemical compounds or materials suitable for oral administration and having a pharmacological action.

The present invention relates to cough/cold pharmaceutical compositions comprising at least one pharmaceutical active having an undesirable taste, a phosphorylated amino acid, and pharmaceutically-acceptable carrier materials suitable for oral or nasal administration. Suitable pharmaceutically acceptable active materials or compounds useful for treating cough, cold, cold-like, allergy and/or flu symptoms are well known, and may be selected from, but are not limited to, an active having analgesic, anti-inflammatory, antipyretic, anesthetic, antihistamine, bronchodilators, decongestant, cough suppressant, demulcents, antitussive, and/or expectorant properties. These actives, as well as their acceptable dosage ranges are described in U.S. Pat. No. 4,783,465 to Sunshine et al., issued Nov. 8, 1988; U.S. Pat. No. 4,619,934 to Sunshine et al., issued Oct. 28, 1986; and *Remington's Pharmaceutical Sciences*, pp. 734–789, 791–799, 861–868, 907–945, 875–888, 1002–1034, 1098–1121, 1124–1131, 1173–1224, 1232–1241 (Alfonso R. Gennaro, editor) (18th ed. 1990), all of which are incorporated by reference herein.

Examples of said decongestants having an undesirable taste include pseudoephedrine, phenylpropanolamine, phenylephrine and ephedrine, their pharmaceutically acceptable salts, and mixtures thereof.

Examples of said antitussives having an undesirable taste include dextromethorphan, chlopedianol, carbetapentane, caramiphen, noscapine, diphenhydramine, codeine, hydrocodone, hydromorphone, their pharmaceutically acceptable salts, and mixtures thereof.

Examples of said expectorants (also known as mucolytic agents) having an undesirable taste include guaifenesin, terpin hydrate, ammonium chloride, N-acetylcysteine, and ambroxol, their pharmaceutically acceptable salts, and mixtures thereof.

Examples of said analgesics having an undesirable taste include morphine, codeine, meperidine, pentazocine, propoxyphene, acetaminophen, allopurinol, acetylsalicylic acid, choline salicylate, ketoprofen, magnesium silicate, fenoprofen, ibuprofen, flurbiprofen, indomethacin, naproxen, and many others, their pharmaceutically acceptable salts, and mixtures thereof.

Examples of said antihistamines having an undesirable taste include brompheniramine, chlorpheniramine, clemastine, dexchlorpheniramine, diphenhydramine, doxylamine, promethazine, terfenadine, triprolidine, and many others, their pharmaceutically acceptable salts, and mixtures thereof.

Typically, the pharmaceutical cough/cold active(s) comprise from about 0.001% to about 99.9%, preferably from about 0.001% to about 75%, and most preferably from about 0.01% to about 30% by weight, of the pharmaceutical compositions of the present invention.

The choice of pharmaceutically-acceptable carrier materials to be used in conjunction with the pharmaceutical cold active of the present compositions is basically determined by the dose form for the compositions. The preferred dosage forms are liquid solutions, liquid suspensions, tablets, capsules and the like, comprising a safe and effective amount of the pharmaceutical actives. Pharmaceutically-acceptable carrier materials and excipients suitable for the preparation of dosage forms for oral and nasal (e.g., nasal sprays) administration are well-known in the art and specific examples are described in U.S. Pat. No. 3,903,297, to Robert, issued Sep. 2, 1975, incorporated by reference herein. Preferably the present invention compositions comprise from about 0.1% to about 99.99% of one or more pharmaceutically-acceptable carrier materials.

Other optional ingredients well known to the pharmacist's art may also be included in amounts generally known for these ingredients. A preferred nonessential component of the present invention is a cooling agent or a combination of cooling agents. Suitable cooling agents are those described in U.S. Pat. No. 4,136,163, issued Jan. 23, 1979, to Watson et al., U.S. Pat. Nos. 4,032,661 and 4,230,688, Jun. 28, 1977 and Oct. 28, 1980, respectively, issued to Rowsell et al. and U.S. Pat. No. 5,266,592, issued Nov. 30, 1993, to Grub et al., all of which are herein incorporated by reference. Particularly preferred cooling agents include N-ethyl-p-menthane-3-carboxamide taught by the above incorporated U.S. Pat. No. 4,136,163 and N,2,3-trimethyl-2-isopropylbutanamide which is taught by the above incorporated U.S. Pat. No. 4,230,688. Another particularly preferred cooling agent is 3-1-menthoxypropane-1,2-diol. This material is described in detail in U.S. Pat. 4,459,425, Jul. 10, 1984 to Amano et al. and incorporated herein by reference. Another preferred optional component is also caffeine.

The present invention further relates to dental compositions such as dentifrices, mouthwashes, and the like, comprising at least one dental active having an undesirable taste, a phosphorylated amino acid, and orally-acceptable carrier materials. The dental actives comprise a safe and effective amount of anticalculus agents, anticaries agents, antimicrobial/antiplaque agents, antibacterial agents, anti-inflammatory agents, surfactants, nutrients, and the like. Typical examples of anticalculus agents include, but are not limited to, those disclosed in U.S. Pat. No. 4,590,066 issued to Parran & Sakkab on May 20, 1986; U.S. Pat. No. 3,429,963 issued to Shedlovsky on Feb. 25, 1969, and U.S.

Pat. No. 4,304,766 issued to Chang on Dec. 8, 1981, and U.S. Pat. No. 4,661,341 issued to Benedict & Sunberg on Apr. 28, 1987; U.S. Pat. No. 4,846,650 issued to Benedict, Bush & Sunberg on Jul. 11, 1989; British Patent No. 490,384 dated Feb. 15, 1937; U.S. Pat. No. 3,678,154 issued to Widder & Briner on Jul. 18, 1972; U.S. Pat. No. 3,737,533 issued to Francis on Jun. 5, 1973, U.S. Pat. No. 3,988,443 issued to Ploger, Schmidt, Dunker & Gloxhuber on Oct. 26, 1976, and U.S. Pat. No. 4,877,603 issued to Degenhardt & Kozikowski on Oct. 31, 1989; all of these patents are incorporated herein by reference. Mixtures of the above-identified anticalculus agents may also be useful. If present, the anticalculus agents generally comprise from about 0.2% to about 13%, preferably from about 0.4% to about 6% of the compositions of the present invention.

Optional tartar control agents include such known materials as those described for example in U.S. Pat. No. 4,627,977 to Gaffar et al., incorporated herein by reference in its entirety; as well as, e.g., polyamino propane sulfonic acid (AMPS)], zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Typical examples of anticaries agents include, but are not limited to, water-soluble fluoride ion sources. The number of such fluoride ion sources is great and includes those disclosed in U.S. Pat. No. 2,946,735 issued Jul. 26, 1960 to Norris, et al., U.S. Pat. No. 3,535,421 issued Oct. 20, 1970 to Briner & Widder, and U.S. Pat. No. 3,678,154 issued Jul. 18, 1972 to Widder, et al., all of which are incorporated herein by reference. Preferred fluoride ion source materials include: sodium fluoride, potassium fluoride, indium fluoride, and sodium monofluorophosphate and mixtures thereof. Sodium fluoride is the preferred fluoride source. The amount of the fluoride ion source in the oral compositions of the present invention, if present, is preferably sufficient to provide from about 0.005% to about 0.35%, more preferably from about 0.05% to about 0.3% of fluoride ions in the compositions.

Typical examples of antimicrobial/antiplaque agents include, but are not limited to, those described in The Merck Index, 10th ed. (1976), U.S. Pat. No. 3,506,720, and European Patent Application No. 0,251,591 of Beecham Group, PLC, published Jan. 7, 1988, U.S. Pat. No. 4,670,252, U.S. Pat. No. 5,338,537, issued Aug. 8, 1994, to White, et al., and U.S. Pat. No. 5,389,360, issued Feb. 14, 1995, to Mobley, et al., all of which are incorporated herein by reference in their entirety. Typical examples of noncationic water insoluble antimicrobial agents useful in the present dental compositions include halogenated diphenyl ethers, phenolic compounds including phenol and its homologs, mono and polyalkyl and aromatic halophenols, resorcinol and its derivatives, bisphenolic compounds and halogenated salicylanilides, benzoic esters, and halogenated carbanilides. If present, the antimicrobial/antiplaque agents generally comprise from about 0.1% to about 5% by weight of the compositions of the present invention.

Typical examples of antibacterial agents include, but are not limited to, noncationic and substantially water insoluble antibacterial agents. An antibacterial agent which is substantially water insoluble as described herein means that its solubility is less than about 1% by weight in water at 25° C. and may be even less than about 0.1%. If an ionizable group is present, solubility is determined at a pH at which ionization does not occur. Antibacterial agents can be present in an effective antiplaque amount, typically about 0.01% to about 5% by weight of the compositions.

Typical examples of anti-inflammatory agents include, but are not limited to, aspirin, ibuprofen, naproxen, indomethacin, piroxicam, flurbiprofen, meclofenamate sodium, ketoprofen, tenidap, tebufelone, ketorolac, and the like. The typical concentrations of anti-inflammatory agents in the dental compositions of the present invention are from about 0.004% to about 20%, preferably from about 0.02% to about 4%, more preferably from about 0.04% to about 2%, and most preferably from about 0.2% to about 0.8% of the compositions of the present invention.

Typical examples of nutrients include, but are not limited to, folate, retinoids (Vitamin A), Vitamin C, Vitamin E and zinc. If present, the nutrients generally comprise from about 0.001% to about 10% by weight of the compositions of the present invention.

In preparing the dental compositions of the present invention, it is desirable to add one or more orally-acceptable carrier materials to the compositions. Such materials are well known in the art and are readily chosen by one skilled in the art based on the physical and aesthetic properties desired for the composition being prepared. Carrier materials typically comprise from about 79% to about 98%, preferably from about 89% to about 98%, by weight of the compositions.

Examples of typical orally-acceptable carrier materials include thickening materials and/or binders in an amount from about 0.1% to about 5% by weight of the total composition; humectants in an amount from about 0% to about 70%, by weight of the total composition; titanium dioxide in an amount from about 0.25% to about 1% by weight of the total composition; buffering agents in an amount from about 0.5% to about 10% by weight of the total composition; abrasive polishing material such as disclosed in U.S. Pat. No. 3,070,510, Dec. 25, 1962; silica dental abrasives such as described in U.S. Pat. No. 3,538,230, issued Mar. 2, 1970, U.S. Pat. No. 3,862,307, Jun. 21, 1975, and U.S. Pat. No. 4,340,583, Jul. 29, 1982, in an amount from about 6% to 70% by weight of the total composition; flavoring agents in an amount from about 0.001% to about 5% by weight of the total composition; sweetening agents in an amount from about 0.005% to about 5% by weight of the composition; and a cooling agent or a combination of cooling agents such as those described in U.S. Pat. No. 4,136,163, Jan. 23, 1979, to Watson et al., U.S. Pat. Nos. 4,032,661 and 4,230,688, Jun. 28, 1977 and Oct. 28, 1980, respectively, to Rowsell et al. and U.S. Pat. No. 5,266,592, Nov. 30, 1993 to Grub et al., and U.S. Pat. No. 4,459,425, Jul. 10, 1984 to Amano et al. All the aforementioned U.S. patents are incorporated herein by reference.

Sodium bicarbonate may also be added to the dental compositions of the present invention. Sodium bicarbonate, also known as baking soda, is a household product with a variety of uses including use in dentifrices and mouthrinses. It is a white powder that is soluble in water and unless stabilized, tends to release carbon dioxide in an aqueous system. The present compositions can contain from about 1% to about 50%, sodium bicarbonate by weight of the total composition.

Likewise, the dental compositions of the present invention may also contain solubilizing agents. Suitable solubilizing agents are used to solubilize the anticalculus agents, anticaries agents, antimicrobial/antiplaque agents, antibacterial agents, anti-inflammatory agents, and do not adversely affect the activity of the anticalculus agents, anticaries agents, antimicrobial/antiplaque agents, antibacterial agents, anti-inflammatory agents used in the compositions. Solubilizing agents are typically used at a level of from about 0.05% to about 10% by weight of the total composition.

The dental compositions of the present invention may also comprise a surfactant, such as those which are reasonably stable and preferably form suds through the pH range of the compositions. Surfactants useful as sudsing agents may be soaps, and anionic, nonionic, cationic, zwitterionic and amphoteric organic synthetic detergents, and compatible mixtures thereof. Surfactants of these types are described more fully in U.S. Pat. No. 3,959,458 issued to Agricola, Briner, Granger & Widder on May 25, 1976, incorporated herein by reference. Such surfactants are generally present in the compositions of the present invention at a level of from about 0% to about 10%, preferably from about 0.2% to about 5%. Surfactants may also be used as solubilizing agents to help retain sparingly soluble components, e.g., some flavoring agents, in solutions. Surfactants suitable for this purpose include polysorbates and poloxamers.

Water may also be present in the dental compositions of the present invention. Water employed in the preparation of commercially suitable oral compositions should preferably be deionized and free of organic impurities. Water generally comprises from about 2% to about 99%, preferably from about 20% to about 95%, by weight of the dental compositions herein. When in the form of toothpastes, the compositions preferably are from about 2% to about 45%, more preferably from about 30% to about 40%, water, while mouthwashes are preferably from about 45% to about 95%, more preferably from about 75% to about 90%, water. These amounts of water include the free water which is added plus that which is introduced with other materials such as with sorbitol.

The dental compositions of the present invention can be in the form of a mouth rinse or liquid dentifrice where conventional mouth rinse components comprise the carrier materials of the present invention. Mouth rinses and liquid dentifrices generally comprise from about 20:1 to about 2:1 of a water ethyl alcohol or alcohol free solution, and preferably other ingredients such as flavors, sweeteners, humectants, and surfactants such as those mentioned above. The humectants, such as glycerin and sorbitol give a moist feel to the mouth. Generally on a weight basis, the mouth rinses and liquid dentifrices of the present invention comprise from about 0% to about 60% ethyl alcohol, from about 0% to about 20% humectant, from about 0% to about 2% surfactant, from about 0% to about 0.5% sweetening agent, from about 0% to about 0.3% flavoring agent and the balance water. Other optional components described herein for use in toothpaste products are also useful in the mouth rinse and liquid dentifrice compositions.

The present invention further relates to compositions for treating upper gastrointestinal tract distress comprising at least one pharmaceutical agent useful for treating upper gastrointestinal tract distress and having an undesirable taste, a phosphorylated amino acid, and pharmaceutically-acceptable carrier material suitable for oral administration. Pharmaceutical actives useful for treating upper gastrointestinal tract distress are those materials which are safe and effective when administered orally for treating disorders of the upper gastrointestinal tract (typically the stomach and/or esophagus) which result in symptoms of upper gastrointestinal tract distress (e.g., heartburn, stomachache, indigestion). Such actives include antacid agents and acid secretion prevention agents (e.g., H2 receptor-blocking antisecretory agents). Antacid agents include, for example, aluminum carbonate, aluminum hydroxide, aluminum phosphate, aluminum hydroxy-carbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumino silicates, magnesium carbonate, magnesium glycinate, magnesium hydroxide, magnesium oxide, magnesium trisilicate, sucralfate, and mixtures thereof. Examples of acid secretion prevention agents include cimetidine, ranitidine, famotidine, omeprazole, and mixtures thereof. Other useful pharmaceutical actives include bismuth-containing agents such as, for example, bismuth subsalicylate, bismuth aluminate, bismuth citrate, bismuth subcitrate, bismuth nitrate, bismuth subcarbonate, bismuth subgalate, and mixtures thereof; anticholinergics such as atropine, clidinium and dicyclomine; laxatives such as phenolphthalein and casanthrol; and antidiarrheals such as diphenoxylate and loperamide. Typically the pharmaceutical active(s) comprise from about 1% to about 99%, by weight, of the pharmaceutical compositions of the present invention, preferably from about 25% to about 60%, and most preferably from about 30% to about 50%.

The choice of pharmaceutically-acceptable carrier and excipient materials to be used in conjunction with the pharmaceutical active useful for treating upper gastrointestinal tract distress of the present compositions is basically determined by the dose form for the compositions. The preferred dosage forms are liquid solutions, liquid suspensions, swallowable tablets and capsules, chewable tablets, and the like, comprising a safe and effective amount of the pharmaceutical actives. Pharmaceutically-acceptable carrier and excipient materials suitable for the preparation of dosage forms for oral administration are well-known in the art. Their selection will depend on secondary considerations like taste, cost, shelf stability, which are not critical for the purposes of the present invention, and can be made without difficulty by a person skilled in the art.

Some examples of substances which can serve as excipients of the pharmaceutically-acceptable carrier materials are sugars such as lactose, glucose and sucrose; starches such as corn-starch and potato starch; cellulose and its derivatives such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobroma; polyols such as propylene glycol, glycerine, sorbitol, mannitol, and polyethylene glycol; agar; and alginic acid; as well as other non-toxic compatible substances used in pharmaceutical formulations. Wetting agents and lubricants such as sodium lauryl sulfate, as well as coloring agents, flavoring agents, sweetening agents (including nonnutritive sweeteners such as aspartame and saccharin), tableting agents, stabilizers, antioxidants, cooling agents, and preservatives, can also be present. Another optional component is also caffeine. Other compatible pharmaceutical additives and actives which are not typical pharmaceutical actives useful for treating upper gastrointestinal tract distress (e.g., NSAID drugs; pain killers; muscle relaxants) may also be included in the compositions of the present invention.

The pharmaceutically-acceptable carrier materials employed in the present ingestible compositions are used at concentrations sufficient to provide a practical size to dosage relationship. Typically, pharmaceutically-acceptable carrier materials comprise from about 1% to about 99% by weight of the pharmaceutical compositions useful for treating upper gastrointestinal tract distress of the present invention, preferably from about 40% to about 75%, and most preferably from about 50% to about 70%. Additionally, the cooling agent or combination of cooling agents typically comprises from about 0.01% to about 0.50% by weight of the pharmaceutical compositions useful for treating upper gastrointestinal tract distress of the present invention, preferably from about 0.02% to about 0.20%, and most preferably from about 0.04% to about 0.10%.

The phosphorylated amino acids may also be added to similar compositions comprising such pharmaceutical actives as laxatives and antidiarrheals, as well as compositions comprising anorexiants, anticholinergics, and antinauseants.

The undesirable taste of other basic pharmaceutically active acid addition salts such as strychnine, quinine, papaverine, berberine, promethazine, brucine, propranolol, and chlorpromazine may also be suppressed by addition of the phosphorylated amino acids of the invention. Inorganic acid salts and organic acid salts such as hydrochloride, nitrate, sulfate, acetate, citrate, and carbonate of basic pharmaceutically active components may also be included. The pharmaceuticals can be in any preparation forms such as solid preparations (e.g., capsule, granules, medicinal pill, powder, pellet, troche and dry syrup); and liquid preparations (e.g., liquids, extracts, elixirs, spirits, syrups, aromatic water, lemonades, and fluid-extracts). The phosphorylated amino acids can be incorporated into the pharmaceutical preparation in any conventional manner. For instance, the phosphorylated amino acids can be incorporated into the pharmaceutical preparation singly or in combination with one or more of known additives. Examples of such known additives include, but are not limited to, diluent, filler, excipient, vehicle, binder, disintegrator, lubricant, fluidity-improving agent, coating agent, flavor, masking agent, perfume, and anti-oxidation agent. The pharmaceutical preparation can be produced using any conventional means. Typically, inhibition of undesirable taste is achieved by the addition of the phosphorylated amino acid comprising from about 0.001% to about 10% by weight, preferably from about 0.01% to about 8% by weight, more preferably from about 0.1% to about 5% by weight, and most preferably from about 0.5% to about 2% by weight, of pharmaceutical compositions having an undesirable taste.

The phosphorylated amino acids can be coated on a composition having a bitter taste. For instance, foods in the form of a solid, such as candy, other confectioneries, processed fish/meats, vegetables, fruits, processed vegetables, processed fruits, dried vegetable juices, and dried fruits juices and pharmaceutical preparations in the form of powder, granules, pellets, tablets, soft and hard capsules, and pills. The coating layer can comprise the phosphorylated amino acid and hydrophilic polymers such as cellulose derivatives, gelatin, and polyvinyl alcohol. Other additives such as sweeteners and flavors can be incorporated into the coating layer. There is no need of coating the whole surface of the material. Partial coating may also be employed. The coating comprising the phosphorylated amino acids can be made on the composition which already contains the phosphorylated amino acids. For the coating, any known coating methods and coating apparatuses can be used.

EXAMPLES

The following examples further describe and demonstrate embodiments within the scope of the present invention. These examples are given solely for the purpose of illustration and are not to be construed as a limitation of the present invention as many variations thereof are possible without departing from the spirit and scope.

EXAMPLES 1-2

Liquid cough/cold compositions for oral administration are prepared by combining the following ingredients:

| Ingredient | % W/V | |
|---|---|---|
| | Ex. 1 | Ex. 2 |
| Ibuprofen Arginate | 1.00 | — |
| Acetaminophen | — | 1.00 |
| Dextromethorphan HBr | — | 0.15 |
| Chlorpheniramine Maleate | 0.02 | 0.02 |
| Pseudoephedrine HCl | 0.30 | 0.30 |
| Phosphotyrosine | 2.00 | 2.00 |
| Alcohol (95%) | 25.00 | 25.00 |
| Propylene Glycol | 25.00 | 25.00 |
| Sodium Citrate | 2.00 | 2.00 |
| Citric Acid | 0.25 | 0.25 |
| Liquid Sugar (Simple Syrup) | 25.00 | 25.00 |
| Glycerin | 7.00 | 7.00 |
| Colorants | 0.008 | 0.008 |
| Flavor | 0.50 | 0.50 |
| Water, Purified | Q.S. | Q.S. |

The purified water (approximately 10% of the final batch volume) is poured into a batch container equipped with a lightnin' mixer. The sodium citrate, citric acid, pseudoephedrine HCl and chlorpheniramine maleate are added sequentially and dissolved with agitation. The glycerin, phosphorylated amino acid, and liquid sugar are then added. In a separate container the colorants are added to purified water (approximately 0.5% of the final batch volume). This colorant solution is then added to the first batch container. In a separate container the ibuprofen arginate, acetaminophen, and/or dextromethorphan are added to the alcohol while stirring. The propylene glycol and flavors are added to this alcohol premix and the resulting mixture is stirred until homogeneous and then added to the first container. The remaining purified water is added to the resulting mixture and stirred.

EXAMPLE 3

A liquid cough/cold composition for oral administration is prepared by combining the following ingredients:

| Ingredient | Amount/15 ml dose |
|---|---|
| Dextromethorphan HBr | 20 mg |
| Glyceryl Guaiacolate | 200 mg |
| Phosphotyrosine | 360 mg |
| Sucrose | 8.16 grams |
| Alcohol | 1 ml |
| Citric Acid, Anhydrous | 4 mg |
| Sodium Citrate | 300 mg |
| MPD[1] | 15 mg |
| WS-3[2] | 0.75 mg |
| Menthol | 7.5 mg |
| Coloring Agent | 4.5 mg |
| Water, Purified | Q.S. to 15 ml |

[1] 3-1-menthoxy propane 1,2-diol, supplied by Takasago Perfumery Co., Ltd., Tokyo, Japan
[2] N-ethyl-p-menthane-3-carboxamide, supplied by Sterling Drugs This composition is prepared by first dissolving the dextromethorphan and glyceryl guaiacolate in alcohol and then adding with constant mixing the menthol, MPD and WS-3. In separate containers dissolve the sucrose in a small portion of the water, dissolve the coloring agent in a separate small portion of the water, and in still another container dissolve the sodium citrate and citric acid in a small portion of the water. Finally, all the premixes, phosphorylated amino acid, and the remaining water are mixed with constant mixing to prepare a composition of the present invention having 20 mg of dextromethorphan and 200 mg of glyceryl guaiacolate per 15 ml of composition.

EXAMPLES 4–7

Given below are four dentifrice examples representative of the present invention.

| Component | Weight % | | | |
|---|---|---|---|---|
| | Ex. 4 | Ex. 5 | Ex. 6 | Ex. 7 |
| Sorbitol (70% Solution) | 61.827 | 51.827 | 47.891 | 41.328 |
| Glycerin | — | 10.000 | 10.198 | 10.000 |
| Glycine | 0.218 | 0.262 | — | — |
| Copper (II) Sulfate-5H$_2$O | 0.360 | 0.360 | — | — |
| Sodium Fluoride | 0.243 | 0.243 | — | — |
| Sodium Carrageenan | — | — | — | 0.350 |
| Magnesium Alumina silicate | — | — | 0.408 | — |
| Sodium Gluconate | — | — | 0.632 | 5.514 |
| Stannous Fluoride | — | — | 0.454 | 0.454 |
| Stannous Chloride dihydrate | — | — | — | 2.198 |
| Stannous Pyrophosphate | — | — | 1.040 | — |
| Sodium Alkyl Sulfate (28% Solution) | 4.000 | 4.000 | 4.000 | 4.000 |
| Phosphoserine | 2.00 | 2.00 | 2.00 | 2.00 |
| Sodium Hydroxide | — | — | 0.200 | 0.850 |
| Saccharin | 0.130 | 0.130 | 0.200 | 0.230 |
| Titanium Dioxide | 0.525 | 0.525 | 0.525 | 0.525 |
| FD&C Blue | 0.050 | 0.050 | 0.051 | 0.051 |
| Silica | 20.000 | 20.000 | 20.000 | 20.000 |
| Carboxy Methyl Cellulose | — | — | 1.050 | 1.000 |
| Xanthan Gum | 0.475 | 0.475 | — | — |
| Carbopo 956* | 0.300 | 0.300 | — | — |
| Flavor | 0.900 | 0.900 | 0.851 | 1.000 |
| Water | Q.S. | Q.S. | Q.S. | Q.S. |

EXAMPLE 8

Given below is a dentifrice example representative of the present invention.

| Component | Weight % Ex. 8 |
|---|---|
| Sorbitol | 35.341 |
| Stannous Fluoride | 0.454 |
| Sodium Gluconate | 4.164 |
| Stannous Chloride | 2.086 |
| AHP | 1.5 |
| Phosphoserine | 2.0 |
| Saccharin | 0.455 |
| Titanium Dioxide | 1 |
| Sodium Hydroxide | 0.75 |
| Silica | 20 |
| Synthetic sodium alkyl sulfate | 4 |
| Glycerin | 10 |
| Xanthan gum | 0.5 |
| Hydroxy ethyl cellulose | 0.75 |
| Flavor | 1 |
| Water-USP Purified | Q.S. |

EXAMPLES 9–10

The following are mouthrinse compositions representative of the present invention.

| Component | Weight % | |
|---|---|---|
| | Ex. 9 | Ex. 10 |
| Stannous Fluoride | 0.100 | 0.100 |
| Stannous Chloride | 0.375 | 0.550 |
| Dihydrate Sodium Gluconate | 1.041 | 0.690 |
| Glycerin | 10.000 | — |
| Phosphoserine | 2.00 | 2.00 |
| Sorbitol (70% aqueous solution) | — | 10.000 |
| Ethanol | 10.000 | 10.000 |
| Polysorbate 80 | 0.300 | — |
| Sorbitan Diisostearate | — | 0.200 |
| Sodium Saccharin | 0.050 | 0.050 |
| Flavor | 0.150 | 0.150 |
| Sodium Hydroxide (50%) | 0.020 | 0.020 |
| Benzoic Acid | 0.050 | 0.050 |
| FD&C Blue #1 (1% solution) | 0.020 | 0.020 |
| Water | Q.S. | Q.S. |

EXAMPLE 11

An ingestible pharmaceutical composition according to the present invention in the form of a chewable antacid tablet is prepared as follows:

| Ingredients | Weight % |
|---|---|
| Granulated calcium carbonate[1] | 42.87% |
| Magnesium stearate | 2.50% |
| Colored speckles | 0.75% |
| Flavorants | 0.78% |
| MPD[2] | 0.07% |
| WS-3[3] | 0.05% |
| Aspartame | 0.198% |
| Sodium Saccharin | 0.102% |
| Phosphotyrosine | 0.5% |
| Mannitol[4] | Q.S. |

[1] Granulated calcium carbonate containing 93.3% calcium carbonate, 6.3% glucose and 0.4% gelatin; supplied by Whittaker Clark & Daniels, Philadelphia, Pa.
[2] 3-1-menthoxy propane-1,2-diol, supplied by Takasago Perfumery Co., Ltd., Tokyo, Japan.
[3] N-ethyl-p-menthane-3-carboxamide, supplied by Sterling Drugs.
[4] Granulate mannitol supplied by ICI Americas, Inc., Wilmington, Delaware.

The above ingredients are dry blended in a mixer until homogeneous, and then direct compressed in a tableting machine to approximately 8.5 Strong Cobb units hardness to produce chewable antacid tablets each weighing 1.25 g (500 mg calcium carbonate per tablet). Ingestion of one or two of these tablets by a human subject suffering from heartburn, acid indigestion and upset stomach associated with these symptoms provides a pleasant tasting and effective relief for this upper gastrointestinal tract distress.

What is claimed is:

1. A method of inhibiting an undesirable taste, wherein said taste is unwanted in oral compositions, such compositions being selected from the group consisting of phosphotyrosine, phosphoserine, phosphothreonine, peptides thereof, enantiomers and racemic mixtures thereof, physiologically acceptable salts thereof, esters thereof, and derivatives thereof comprising alkyl chains, acyl chains, aryl groups, and substitutions containing halogen, thio, cyano, and nitro groups, to said compositions, said containing halogen, thio, cyano, and nitro groups, to said compositions, said undesirable taste is selected from the group consisting of sweet bitter, sour, salty, alkaline, astringent, tangy, sharp, acidic, spicy, pungent, woody, smoky, umami, metallic, any aftertaste, and mixtures thereof.

2. A method according to claim 1 wherein said oral compositions are selected from the group consisting of foods, drinks, pharmaceuticals, toiletries, and mixtures thereof.

3. A method according to claim 2 wherein said undesirable taste is selected from the group consisting of bitter, metallic, and mixtures thereof.

4. A method according to claim 3 wherein said taste is provided by at least one orally administrable pharmaceutical active selected from the group consisting of bronchodilators, anorexiants, antihistamines, nutritional supplements, laxatives, analgesics, anesthetics, antacids, H2-receptor antagonists, anticholinergics, antidiarrheals, decongestants, demulcents, antitussives, antinauseants, antimicrobials, antibacterials, antifungals, antivirals, expectorants, anti-inflammatory agents, antipyretics, and mixtures thereof.

5. A method according to claim 1 wherein said phosphorylated amino acid is selected from the group consisting of phosphotyrosine, phosphoserine, phosphothreonine, and mixtures thereof.

6. A method according to claim 5 wherein said phosphorylated amino acid is phosphotyrosine.

7. A pharmaceutical composition comprising at least one orally administratable pharmaceutical active having an undesirable taste, wherein said taste is unwanted in oral compositions having said undesirable taste, and a phosphorylated amino acid selected from the group consisting of phosphotyrosine, phosphoserine, phosphothreonine, peptides thereof, enantiomers and racemic mixtures thereof, physiologically acceptable salts thereof, esters thereof, and derivatives thereof comprising akyl chains, acyl chains, aryl groups, and substitutions containing halogen, thio, cyano, and nitro groups, said undesirable taste is selected from the group consisting of sweet, bitter, sour, salty, alkaline, astringent, tangy, dry, sharp, cool, hot, burning, acidic, spicy, pungent, woody, smoky, umami, metallic, any aftertaste, and mixtures thereof.

8. A pharmaceutical composition according to claim 7 wherein said pharmaceutical active is selected from the group consisting of decongestants, expectorants, antitussives, antihistamines, bronchodilators, demulcents, anti-inflammatory agents, antipyretics, analgesics, anesthetics, antimicrobials, antibiotics, peroxides, antibacterials, anticalculus agents, anticaries agents, nutrients, antacids, H2-receptor antagonists, laxatives, antidiarrheals, anorexiants, anticholinergics, antinauseants, and mixtures thereof.

9. A pharmaceutical composition according to claim 7 wherein said composition is selected from the group consisting of a treatment for cough/cold symptoms, a dentifrice, a mouthrinse, and a treatment for gastrointestinal distress.

10. A pharmaceutical composition according to claim 9 wherein said composition is a treatment for cough/cold symptoms comprising at least one orally administratable pharmaceutical active having an undesirable taste selected from the group consisting of decongestants, expectorants, antitussives, antihistamines, bronchodilators, demulcents, anti-inflammatory agents, antipyretics, analgesics, anesthetics, and mixtures thereof and said phosphorylated amino acid is selected from the group consisting of phosphotyrosine, phosphoserine, phosphothreonine, and mixtures thereof.

11. A pharmaceutical composition according to claim 10 wherein said phosphorylated amino acid is phosphotyrosine.

12. A pharmaceutical composition according to claim 9 wherein said composition is a dentifrice comprising at least one orally administratable pharmaceutical active having an undesirable taste selected from the group consisting of anti-inflammatory agents, antimicrobials, antibiotics, peroxides, antibacterials, anticalculus agents, anticaries agents, nutrients and said phosphorylated amino acid is selected from the group consisting of phosphotyrosine, phosphoserine, phosphothreonine, and mixtures thereof.

13. A pharmaceutical composition according to claim 12 wherein said phosphorylated amino acid is phosphotyrosine.

14. A pharmaceutical composition according to claim 9 wherein said composition is a treatment for gastrointestinal distress comprising at least one orally administratable pharmaceutical active having an undesired taste selected from the group consisting of antacids, H2-receptor antagonists, laxatives, antidiarrheals, and mixtures thereof and said phosphorylated amino acid is selected from the group consisting of phosphotyrosine, phosphoserine, phosphothreonine, and mixtures thereof.

15. A pharmaceutical composition according to claim 14 wherein said phosphorylated amino acid is phosphotyrosine.

* * * * *

UNITED STATES PATENT AND TRADEMARK OFFICE
CERTIFICATE OF CORRECTION

PATENT NO. : 5,766,622
DATED : June 16, 1998
INVENTOR(S) : Sandra Lynn Nelson

It is certified that error appears in the above-identified patent and that said Letters Patent is hereby corrected as shown below:

Please rewrite Claim 1 as follows:

1. A method of inhibiting an undesirable taste[, wherein said taste is unwanted in oral compositions, such compositions selected from the group consisting of phosphotyrosine, phosphoserine, phosphothreonine, peptides thereof, enantiomers and racemic mixtures thereof, physiologically acceptable salts thereof, esters thereof, and derivatives thereof comprising akyl chains, acyl chains, aryl groups, and substitutions containing halogen, thio, cyano, and nitro groups, to said compositions, said undesirable taste is selected from the group consisting of sweet, bitter, sour, salty, alkaline, astringent, tangy, sharp, acidic, spicy, pungent, woody, smoky, umami, metallic, any aftertaste, and mixtures thereof] _in oral compositions having said undesirable taste, wherein said compositions are selected from the group consisting of foods, drinks, pharmaceuticals, toiletries, and mixtures thereof and wherein said undesirable taste is selected from the group consisting of sweet, bitter, sour, salty, alkaline, astringent, tangy, sharp, acidic, spicy, pungent, woody, smoky, umami, metallic, any aftertaste, and mixtures thereof, and wherein said taste is unwanted in said oral compositions; said method comprising the addition of a phosphorylated amino acid to said compositions having said undesirable taste, wherein said phosphorylated amino acid is selected from the group consisting of phosphotyrosine, phosphoserine, phosphothreonine, peptides thereof, enantiomers and racemic mixtures thereof, physiologically acceptable salts thereof, esters thereof, and derivatives thereof comprising alkyl chains, acyl chains, aryl groups, and substitutions containing halogen, thio, cyano, and nitro groups._

Cancel claims 2 and 5.

UNITED STATES PATENT AND TRADEMARK OFFICE
CERTIFICATE OF CORRECTION

PATENT NO. : 5,766,622
DATED : June 16, 1998
INVENTOR(S) : Sandra Lynn Nelson

It is certified that error appears in the above-identified patent and that said Letters Patent is hereby corrected as shown below:

Please rewrite Claim 3 as follows:

2. A method according to Claim [2] 1 wherein said undesirable taste is selected from the group consisting of bitter, metallic, and mixtures thereof.

Please rewrite Claim 6 as follows:

4. A method according to Claim [5] 1 wherein said phosphorylated amino acid is phosphotyrosine.

Please add, column 13, after line 30, -- * Carboxyvinyl polymer supplied by B. F. Goodrich Company. --.

Signed and Sealed this

Twenty-third Day of March, 1999

Attest:

Q. TODD DICKINSON

*Attesting Officer*    *Acting Commissioner of Patents and Trademarks*